US008859593B2

(12) United States Patent
Zisapel et al.

(10) Patent No.: US 8,859,593 B2
(45) Date of Patent: Oct. 14, 2014

(54) COMPOSITION FOR IMPROVING COGNITION AND MEMORY

(75) Inventors: Nava Zisapel, Tel Aviv (IL); Moshe Laudon, Kfar Saba (IL)

(73) Assignee: Neurim Pharmaceuticals (1991) Ltd., Tel Aviv (IL)

(*) Notice: Subject to any disclaimer, the term of this patent is extended or adjusted under 35 U.S.C. 154(b) by 2330 days.

(21) Appl. No.: 10/555,011

(22) PCT Filed: Apr. 15, 2004

(86) PCT No.: PCT/IL2004/000330
§ 371 (c)(1),
(2), (4) Date: Oct. 31, 2005

(87) PCT Pub. No.: WO2004/096118
PCT Pub. Date: Nov. 11, 2004

(65) Prior Publication Data
US 2006/0229340 A1 Oct. 12, 2006

(30) Foreign Application Priority Data
Apr. 29, 2003 (IL) .......................................... 155666

(51) Int. Cl.
| A61K 31/4439 | (2006.01) |
| A61K 31/405 | (2006.01) |
| A61K 9/70 | (2006.01) |
| A61K 9/20 | (2006.01) |
| A61K 45/06 | (2006.01) |
| A61K 31/465 | (2006.01) |
| A61K 31/4045 | (2006.01) |

(52) U.S. Cl.
CPC ............. *A61K 9/7061* (2013.01); *A61K 9/2009* (2013.01); *A61K 45/06* (2013.01); *A61K 9/2027* (2013.01); *A61K 31/465* (2013.01); *A61K 31/4045* (2013.01)
USPC .......................................... 514/343; 514/419

(58) Field of Classification Search
USPC .................................................. 514/343, 419
See application file for complete search history.

(56) References Cited

U.S. PATENT DOCUMENTS

| 4,680,172 A | 7/1987 | Leeson |
| 4,765,985 A | 8/1988 | Leeson |
| 4,965,074 A | 10/1990 | Leeson |
| 5,284,660 A | 2/1994 | Lee et al. |
| 5,508,039 A | 4/1996 | Yates et al. |
| 5,641,801 A | 6/1997 | Wurtman |
| 5,700,828 A | 12/1997 | Federowicz et al. |
| 5,750,557 A | 5/1998 | Zisapel |
| 5,872,101 A | 2/1999 | Munoz et al. |
| 6,068,853 A | 5/2000 | Giannos et al. |
| 6,069,138 A | 5/2000 | Ponroy |
| 6,183,775 B1 | 2/2001 | Ventouras |
| 6,353,015 B1 * | 3/2002 | Oxenkrug et al. ............ 514/415 |
| 6,353,051 B1 | 3/2002 | Huang |
| 6,486,172 B2 * | 11/2002 | Myers et al. .................. 514/305 |
| 2001/0029959 A1 | 10/2001 | Burgard et al. |
| 2003/0051728 A1 | 3/2003 | Lloyd et al. |
| 2003/0062042 A1 | 4/2003 | Wensley et al. |
| 2004/0096118 A1 | 5/2004 | Liang |

FOREIGN PATENT DOCUMENTS

| EP | 0197390 A2 | 10/1986 |
| EP | 1272177 B1 | 1/2003 |
| EP | 1304048 A1 | 4/2003 |
| RU | 2134108 C1 | 8/1999 |
| WO | 8803803 A1 | 6/1988 |
| WO | WO 8803803 A1 | 6/1988 |
| WO | 9307870 A1 | 4/1993 |
| WO | WO 9307870 A1 | 4/1993 |
| WO | 9427576 A1 | 12/1994 |
| WO | WO 9427576 A1 | 12/1994 |
| WO | 9501766 A1 | 1/1995 |
| WO | WO 9501766 A1 | 1/1995 |
| WO | 9623496 A1 | 8/1996 |
| WO | WO 9623496 A1 | 8/1996 |
| WO | 9632947 A1 | 10/1996 |
| WO | WO 9632947 A1 | 10/1996 |
| WO | 9854189 A1 | 12/1998 |
| WO | WO 9854189 A1 | 12/1998 |
| WO | 0045795 A2 | 8/2000 |
| WO | WO 0045795 A2 | 8/2000 |
| WO | 02076211 A1 | 10/2002 |
| WO | WO 02076211 A1 | 10/2002 |

OTHER PUBLICATIONS

Jean-Louis et al. Melatonin effects on sleep, mood, and cognition in elderly with mild cognitive impairment. Journal of Pineal Research 1998, 25 (3), pp. 177-183.*
Araki, H.K., et al., "Neuronal Nicotinic Receptor and Psychiatric Disorders: Functional and Behavioral Effects of Nicotine," *Jpn. J. Pharmacol.*, 2002, pp. 133-138, vol. 88.
Benwell, M.E., et al., "Evidence that tobacco smoking increases the density of (-)(3H)nicotine binding sites in human brain," *Journal of Neurochemistry*, Apr. 1988, pp. 1243-1247, vol. 50, No. 4. Medline Abstract No. NLM3346676.
Dollins, Andrew B., et al., "Effect of pharmacological daytime doses of melatonin on human mood and performance," *Psychopharmacology*, 1993, pp. 490-496, vol. 112.
Gäddnas, Helena, et al., "Pineal melatonin and brain transmitter monoamines in CBA mice during chronic oral nicotine administration," *Brain Research*, 2002, pp. 76-83, vol. 957.

(Continued)

*Primary Examiner* — Jennifer M Kim
(74) *Attorney, Agent, or Firm* — Rothwell, Figg, Ernst & Manbeck, P.C.

(57) ABSTRACT

The invention relates to a pharmacologically active combination, having utility in treating insomnia patients, which comprises: (a) at least one first active ingredient selected from melatonin, other melatonergic agents, melatonin agonists and melatonin antagonists; and (b) at least one second active ingredient selected from nicotine and nicotine receptor agonists; to use of a medicament containing component (a) with or without component (b) for alleviation of at least one adverse effect which occurs in a patient in the course of nicotine replacement therapy, or otherwise, selected from impairment of the quality of sleep, impairment of cognition and impairment of memory, as well as to a kit having utility in treating insomnia patients, which comprises components (a) and (b) in unit dosage form.

10 Claims, No Drawings

(56) References Cited

OTHER PUBLICATIONS

Garfinkel, D., et al., "Improvement of sleep quality in elderly people by controlled-released melatonin," The Lancet, Aug. 26, 1995, pp. 541-544, vol. 346.
Graw, Peter, et al., "Early morning melatonin administration impairs psychomotor vigilance," Behavioral Brain Research, 2001, pp. 167-172, vol. 121.
Haimov, Iris, et al., "Melatonin Replacement Therapy of Elderly Insomniacs," Sleep, 1995, pp. 598-603, vol. 18, No. 7.
Hughes, Rod J., et al., "The Role of Melatonin and Circadian Phase in Age-relaed Sleep-maintenance Insomnia: Assessment in a Clinical Trial of Melatonin Replacement," Sleep, 1998, pp. 52-68, vol. 21, No. 1.
James, Steven P., et al., "The Effect of Melatonin on Normal Sleep," Neuropsychopharmacology, 1987, pp. 41-44, vol. 1, No. 1.
James, Steven P., et al., "Melatonin Administration in Insomnia," Neuropsychopharmacology, 1990, pp. 19-23, vol. 3, No. 1.
Jorenby, Douglas, "Clinical Efficacy of Bupropion in the Management of Smoking Cessation," Drugs, 2002, pp. 25-35, vol. 62 Suppl., No. 2.
Jorenby, Douglas, et al., "A Controlled Trial of Sustained-Release Bupropion, a Nicotine Patch, or Both for Smoking Cessation," 2004, pp. 685-691, vol. 340, No. 9.
Maquet, Pierre, "The Role of Sleep in Learning and Memory," Science, Nov. 2, 2001, pp. 1048-1052, vol. 294.
Markus, Regina, P., et al., "Melatonin Nocturnal Surge Modulates Nicotinic Receptors and Nicotine-Induced [$^3$H]-Glutamate Release in Rat Cerebellum Slices," JPET Fast Forward, Jan. 24, 2003, DOI:10.1124/jpet.102.045625, 29 pages.
Markus, Regina P., et al., "Melatonin Modulation of Presynaptic Nicotinic Acetylcholine Receptors in the Rat Vas Deferens," The Journal of Pharmacology and Experimental Therapeutics, 1996, pp. 18-22, vol. 279.
Parrott, A.C., et al., "The Leeds Sleep Evaluation Questionnaire in Psychopharmacological Investigations—A Review," Psychopharmacology, 1980, pp. 173-179, vol. 71, No. 2.
Pereira, Edna F.R., et al., "Unconventional Ligands and Modulators of Nicotinic Receptors," J. Neurobiol., 2002, pp. 479-500, vol. 53, No. 4.
Picciotto, Marina R., et al., "Nicotinic Receptors in Aging and Dementia," J. Neurobiol., 2002, pp. 641-655, vol. 53, No. 4.
Rezvani, Amir H., et al., "Cognitive Effects of Nicotine," Biol. Psychiatry, 2001, pp. 258-267, vol. 49.
Richardson, C. E., et al., "Effect of smoking and transdermal nicotine on colonic nicotinic acetylcholine receptors in ulcerative colitis," Q J Med, 2003, pp. 57-65, vol. 96.
Rodenbeck, Andrea, et al., "Interactions between evening and nocturnal cortisol secretion and sleep parameters in patients with severe chronic primary insomnia," Neuroscience Letters, 2002, pp. 159-163, vol. 324.
Sherer, Michael A., et al., "Effects of Melatonin on Performance Testing in Patients with Seasonal Affective Disorder," Neuroscience Letters, 1985, pp. 277-282, vol. 58.
Tarquini, Brunetto, et al., "Daytime Circulating Melatonin Levels in Smokers," Tumori, 1994, pp. 229-232, vol. 80.
Vgontzas, Alexandros N., et al., "Chronic Insonmnia Is Associated with Nyctohemeral Activation of the Hypothalamic-pituitary-Adrenal Axis: Clinical Implications," J. Clin. Endocrinol. Metab., 2001, pp. 3787-3794, vol. 86, No. 8.
Wetter, David W., et al., "Tobacco Withdrawal and Nicotine Replacement Influence Objective Measures of Sleep," Journal of Consulting and Clinical Psychology, 1995, pp. 658-667, vol. 63, No. 4.
Woodruff-Pak, Diana S., et al., "Nicotinic Cholinergic Modulation: Galantamine as a Prototype," CNS Drug Reviews, 2002, pp. 405-426, vol. 8, No. 4.
Zhdanova, Irina V., et al., "Melatonin treatment attenuates symptoms of acute nicotine withdrawal in humans," Pharmacology, Biochemistry and Behavior, 2000, pp. 131-135, No. 67.
Slotten, H.A., et al., "Does Melatonin Have an Effect on Cognitive Performance?," Psychoneuroendocrinology, 21(8): 673-680 (1996).
Evans et al., "Evidence for Direct Vasoconstrictor Activity of Melatonin in "Pressurized" Segments of Isolated Caudal Artery from Juvenile Rats", Archives of Pharmacology, 346, 1992, pp. 362-365.
Molinari et al., "2-[125I]iodo-5-methoxycarbonylamino-N-acetyltryptamine: A Selective Radioligand for the Characterization of Melatonin ML2 Binding Sites," Eur J Pharmacol., 301(1-3):159-68, 1996, 1 page.
Staner, et al., "Sleep effects of a 24-h versus a 16-h nicotine patch: A polysomnographic study during smoking cessation," Sleep Med., 7(2): 147-54 (2004).
Slotten, H.A., et al., "Does Melatonin Have an Effect on Cognitive Performance?," Psychoneuroendocrinology, 21 (8): 673-680 (1996).
Rogers, Naomi L., et al., "Neurobehavioural performance effects of daytime melatonin and temazepam administration," J. Sleep Res., 12: 207-212 (2003).
Comperatore, Carlos A., et al., "Aviator's Grounding Time after Melatonin Administration during Rapid Deployment Missions," NATO—RTA—AMP Meeting, Sep. 29-Oct. 3, 1997, Rotterdam.
Wesensten, Nancy Jo, et al., "Daytime Slep and Performance Folloiwng a Zolpidem and Melatonin Cocktail," Sleep, 28(1): 93-103 (2005).
Riemersma-Van Der Lek, Rixt F., et al., "Effect of Bright Light and Melatonin on Cognitive and Noncognitive Function in Elderly Residents of Group Care Facilities," JAMA, 299(22): 2642-2655 (Jun. 11, 2008).
Dineley et al.,"Amino Acid Determinants of Alpha 7 Nicotinic Acetylcholine Receptor Surface Expression", J Biol Chem. 275(18): 13974-85, 2000, 1 page.
Duckles et al., "Melatonin Receptors Potentiate Contractile Responses to Adrenergic Nerve Stimulation in Rat Caudal Artery", Proc. West. Pharmacol. Soc. 38, 1995, pp. 101-102.
Engeland et al., "Nicotine and Sensory Memory in Alzheimer's Disease: An Event-related Potential Study", PubMed, Brain Cogn. 49(2); 2002, pp. 232-234.
Evans et al., "Evidence for Direct Vasoconstrictor Activity of Melatonin in "Pressurized" Segments of Isolated Caudal Artery from Juvenile Rats", Archives of Pharmacology, 346, 1992, pp. 362-365.
Hope et al., "Long-Term Upregulation of Protein Kinase A and Adenylate Cyclase Levels in Human Smokers", The Journal of Neuroscience, 27(8): 2007, pp. 1964-1972.
Levine et al., "Nicotinic Treatment for Cognitive Dysfunction", PubMed, Curr Drug Targets CNS Neurol Disorders, 2002, 1(4): 423-31.
Lin et al., "Structure-activity Studies on 2-methyl-3-(2(S)-pyrrolidinylmethoxy) Pyridine (ABT-089): An Orally Bioavailable 3-pyridyl Ether Nicotinic Acetylcholine Receptor Ligand with Cognition-enhancing Properties", J Med Chem, 40(3), 1997, pp. 385-390.
Luboshizsky et al., "Sleep-inducing Effects of Exogenous Melatonin Administration", Sleep Medicine Reviews, vol. 2, Issue 3, 1998, pp. 191-202.
Molinari et al., "2-[125I]iodo-5-methoxycarbonylamino-N-acetyltryptamine: A Selective Radioligand for the Characterization of Melatonin ML2 Binding Sites, " Eur J Pharmacol., 301(1-3):159-68, 1996, 1 page.
Oxenkrug, Antidepressive and Antihypertensive Effects of MAO-A Inhibition: Role of N-acetylserotonin. A review, Neurobiology (Bp), 7(2): 1997, 1 page.
Rezvani et al., "Cognitive Effects of Nicotine", Society of Biological Psychiatry, 2001, 49:258-267.
Rogers et al., "Potential Action of Melatonin in Insomnia", Sleep, vol. 26, No. 8, 2003, pp. 1058-1059.
Stickgold et al., "Sleep, Learning, and Dreams: Off-line Memory Reprocessing", Science, vol. 294, 2001, 1 page.
Weekley "Effects of Melatonin on Pulmonary and Coronary Vessels are exerted Through Perivascular Nerves", Clinical Autonomic Research 3, 1993, pp. 45-47.
Wetter et al., "Tobacco Withdrawal and Nicotine Replacement Influence Objective Measures of Sleep", Journal of Consulting and Clinical Psychology, vol. 63, No. 4, 1995, pp. 658-667.

* cited by examiner

COMPOSITION FOR IMPROVING COGNITION AND MEMORY

This application is a filing under 35 USC 371 of PCT/IL2004/000330, filed Apr. 15, 2004, which claims priority from IL 155666, filed Apr. 29, 2003.

FIELD OF THE INVENTION

The present invention relates to a pharmacologically active combination, and a kit, having utility in treating insomnia patients, as well as the use of melatonin and related compounds in the manufacture of a medicament which alleviates adverse effects which occur in the course of nicotine replacement therapy.

BACKGROUND OF THE INVENTION

Acetylcholine is a major neurotransmitter in the brain and peripheral nervous systems; it induces a variety of physiological and behavioral responses by binding and activating specific receptors that belong to the muscarinic (defined on the basis of their activation by muscarine) and nicotinic (defined on the basis of their activation by nicotine) acetylcholine receptor families.

Neuronal nicotinic acetylcholine receptors (nAChRs) belong to a family of ligand-gated ion channels that are distributed extensively throughout the central and peripheral nervous systems. The nAChRs are the main mediators of fast synaptic transmission in ganglia, and therefore, are key molecules for the processing of neural information in the autonomic nervous system. The nAChRs are involved in the control of organ systems such as heart, gut, and bladder. In this respect, it is important to note that ulcerative colitis (UC) is a disease largely of non-smokers, in which nicotine is of therapeutic value. The mode of action is unknown, but may involve nicotinic acetylcholine receptors (nAChRs) in the bowel wall (Richardson, C. E., J. M. Morgan, et al. (2003). "Effect of smoking and transdermal nicotine on colonic nicotinic acetylcholine receptors in ulcerative colitis," *Q J Med* 96: 57-65).

In the brain, beyond their role in relation to tobacco use, nAChRs are involved in a wide variety of behavioral functions including cognitive function (Araki, H., K. Suemaru, et al. (2002), "Neuronal Nicotinic Receptor and Psychiatric Disorders: Functional and Behavioral Effects of Nicotine." *Jpn. J. Pharmacol* 88: 133-138). Both acute and chronic nicotine administration significantly improves working memory performance of rats in the radial-arm maze. In humans, activation of nAChRs provides beneficial treatment for cognitive dysfunction such as Alzheimer's disease, schizophrenia, and attention deficit hyperactivity disorder (ADHD). Nicotine has been shown to improve attentional performance in all of these disorders. The nAChRs participate in the pathogenesis of several brain disorders (Parkinson's and Alzheimer's diseases, Tourette's syndrome, schizophrenia, depression, attention deficit disorder). In the same diseases, clinical studies showed that nicotine had beneficial effects, both as a therapeutic and prophylactic agent.

Activation of neuronal nicotinic acetylcholine receptors (nAChRs) has been shown to maintain cognitive function following aging or the development of dementia (Picciotto, M. R. and M. Zoli (2002), "Nicotinic Receptors in Aging and Dementia," *J Neurobiol* 53(4): 641-55). Nicotine and nicotinic agonists have been shown to improve cognitive function in aged or impaired subjects (Rezvani, A. H. and E. D. Levin (2001). "Cognitive Effects of Nicotine," *Biol Psychiatry* 49: 258-267). Smoking has also been shown in some epidemiological studies to be protective against the development of neurodegenerative diseases. This is supported by animal studies that have shown nicotine to be neuroprotective both in vivo and in vitro. Treatment with nicotinic agonists may therefore be useful in both slowing the progression of neurodegenerative illnesses, and improving function in patients with the disease. Nicotine addiction (primarily through tobacco smoking) is a chronic relapsing condition that can be difficult to treat. DSM-IV (Diagnostic and Statistical Manual of Mental Disorders—Fourth Edition, published by the American Psychiatric Association, Washington D.C., 1994) has included a nicotine withdrawal syndrome that is characterized by craving for cigarettes, irritability, anxiety, inner tension, and concentration difficulties. These symptoms are usually observed within the first two weeks after sudden cessation of smoking although some can be experienced as early as 4-6 h after the last cigarette. Nicotine replacement therapy attenuates these symptoms.

Nicotinic acetylcholine receptor pharmacology is becoming increasingly important in the clinical symptomatology of smoking cessation and neurodegenerative diseases in general, and of cognitive and behavioral aspects in particular. Cholinesterase inhibitors (ChEIs) inhibit the degradation of acetylcholine thereby increasing its concentration in the brain. ChEIs are used for the treatment of dementia, by virtue of their ability to increase brain acetylcholine concentrations that subsequently cause activation of nAChRs. In addition, the concept of allosteric modulation of nicotinic acetylcholine receptors has become a research focus for the development of therapeutic agents. Within this context, galantamine, a recently approved drug for cognition enhancement in Alzheimer's disease, modestly inhibits acetylcholinesterase and has an allosteric potentiating ligand effect at nicotinic receptors (Woodruff-Pak, D. S., C. Lander, et al. (2002), "Nicotinic Cholinergic Modulation: Galantamine as a Prototype," *NS Drug Reviews* 8(4): 405-426).

Of major interest, however, is the fact that the activity of the different subtypes of neuronal nAChR is also subject to modulation by substances of endogenous origin such as choline, the tryptophan metabolite kynurenic acid, neurosteroids, and beta-amyloid peptides, and by exogenous psychotomimetic drugs such as phencyclidine and ketamine (Pereira, E. F., C. Hilmas, et al. (2002). "Unconventional Ligands and Modulators of Nicotinic Receptors," *J Neurobiol* 53(4): 479-500). Recently, sustained-release bupropion (bupropion SR) treatment was found efficacious in smoking cessation (Jorenby, D. (2002), "Clinical Efficacy of Bupropion in the Management of Smoking Cessation," *Drugs* 62(2): 25-35).

While nicotinic cholinergic receptors are present in many brain regions, it remains unclear which are important for the effects of nicotine on sleep and daytime alertness, although it is clear that such effects are present. There is also little literature on the effects of nicotine on sleep in non-smokers, while early nicotine withdrawal has been associated with sleep fragmentation in smokers (Wetter, D. W., M. C. Diore, et al. (1995), "Tobacco Withdrawal and Nicotine Replacement Influence Objective Measures of Sleep," *Journal of Consulting and Clinical Psychology* 63(4): 658-667).

One of the significant observed side effects of patch nicotine replacement is insomnia (Jorenby, D. E., S. J. Leischow, et al. (1999), "A Controlled Trial of Sustained-Release Bupropion, A Nicotine Patch, or Both for Smoking Cessation," *The New England Journal of Medicine* 340(9): 685-691). Based on the known stimulating effects of nicotine on cortisol secretion, markedly reduced cortisol concentrations are likely to be a neuroendocrine consequence of abstinence from smoking. Nicotine replacement therapy may activate the HPA axis and increase cortisol levels. Such activation may presumably lead to sleep problems as recent findings suggest that high cortisol levels are associated with poor sleep quality (Rodenbeck, A., G. Huether, et al. (2002), "Interactions between evening and nocturnal cortisol secretion and sleep parameters in patients with severe chronic primary insomnia," *Neuroscience Letters* 324: 159-163; and Vgontzas, A. N., E. O. Bixler, et al. (2001), "Chronic Insomnia Is Associated with Nyctohemeral Activation of the Hypothalamic-Pituitary-Adrenal Axis: Clinical Implications," *J Clin Endocrinol Metab* 86(8): 3787-3794).

Melatonin, the hormone secreted at night by the pineal gland, has sleep promoting properties when given at daytime, namely when its levels in the body are low. The effect observed, shortening of sleep latency, is regarded as evidence of hypnotic activity of a drug (benzodiazepines and non-benzodiazepines), though hypnotic drugs usually impair daytime vigilance. Indeed, melatonin, like hypnotic drugs, produces a significant decrease in vigilance and performance during the first hours after its administration (Wurtman U.S. Pat. No. 5,641,801 Jun. 24, 1997; Graw, P., E. Werth, et al. (2001). "Early morning melatonin administration impairs psychomotor vigilance," *Behavioural Brain Research* 121: 167-172; Dollins, A. B., H. J. Lynch, et al. (1993). "Effect of pharmacological daytime doses of melatonin on human mood and performance," *Psychopharmacology* 112: 490-496).

Moreover, an expert in the field may report that melatonin in fact harms vigilance, as indeed has been found in depressed patients following one week of daily administration of oral melatonin (Sherer, M. A., H. Weingartner, et al. (1985). "Effects of melatonin on performance testing in patients with seasonal affective disorder," *Neuroscience Letters* 58: 277-82). Therefore, at low doses (0.3-10 mg), melatonin's pharmacological activity is regarded as hypnotic. As such, it is not expected to improve psychomotor or cognitive performance shortly after its administration, or improve daytime functioning.

The sleep inducing effects of melatonin at night have been demonstrated in elderly patients with insomnia, in whom melatonin production is low due to aging and diseases, and additional cases in which melatonin deficiency was apparently involved. Administration of melatonin at night (0.3-2 mg daily for 1-3 weeks) improves sleep compared to placebo in elderly subjects with insomnia (Haimov, I., P. Lavie, et al. (1995), "Melatonin replacement therapy of elderly insomniacs," *Sleep* 18(7): 598-603; 18:598-603; Garfinkel, D., M. Laudon, et al. (1995), "Improvement of sleep quality in elderly people by controlled-release melatonin," *The Lancet* 346: 541-544). However, melatonin may be less effective at night in younger patients with insomnia who apparently produce sufficient amounts of melatonin endogenously (James, S. P., D. A. Sack, et al. (1990), "Melatonin administration in insomnia," *Neuropsychopharmacology* 3: 19-23; James, S. P., W. B. Mendelson, et al. (1987). "The effect of melatonin on normal sleep," *Neuropsychopharmacology* 1: 41-44). In a recent study melatonin (0.5 mg) was administered as immediate-release (evening or mid-night administration) or prolonged-release forms (evening administration) to a group of patients with age-related sleep maintenance insomnia. All three melatonin treatments shortened latencies to persistent sleep but was not effective in sustaining sleep (Hughes, R. J., R. Sack, et al. (1998), "The role of melatonin and circadian phase in age-related sleep-maintenance insomnia: assessment in a clinical trial of melatonin replacement," *Sleep* 21(1): 52-68). Therefore, melatonin may not be effective in promoting sleep at night in patients who produce sufficient amounts of the hormone endogenously.

Studies in vivo have failed to demonstrate significant effects of nicotine on the endogenous melatonin production in animals and humans (Tarquini, B., F. Perfetto, et al. (1994), "Daytime circulating melatonin levels in smokers," *Tumori* 80: 229-232; Gaddnas, H., K. Pietila, et al. (2002), "Pineal melatonin and brain transmitter monoamines in CBA mice during chronic oral nicotine administration," *Brain Research* 957: 76-83). Thus, it could not have been inferred that melatonin might alleviate sleep problems associated with nicotine treatment, either in the form of cigarette smoking or upon nicotine replacement therapy for smoking cessation. In one study, administration of exogenous melatonin alone without nicotine replacement therapy, shortly after smoking cessation (4 hours), alleviated symptoms of acute nicotine withdrawal, compared to placebo treated control subjects; administration of melatonin (4 mg, i.p.) was not associated with an increase of a feeling of sedation or fatigue in these subjects (Zhdanova, I. and V. Piotrovskaya (2000), "Melatonin treatment attenuates symptoms of acute nicotine withdrawal in humans," *Pharmacology, Biochemistry and Behavior* 67: 131-135). These data suggest that melatonin alone may alleviate symptoms of smoking cessation, but would not suggest that at the same time it would also be able to alleviate symptoms of nicotine replacement therapy. Since on the one hand, nicotine does not suppress melatonin production, and on the other hand melatonin may not be effective in improving sleep in subjects who produce sufficient amounts of the hormone, and, in addition, any hypnotic activity of melatonin is expected to be associated with a deterioration in cognition and performance, nothing in the available data suggest that melatonin might be a useful agent in alleviating the insomnia incurred by nicotine replacement therapy or that it would enhance the cognitive effects of nicotine.

In Markus, R. P., J. M. Santos, et al. (2003), "Melatonin Nocturnal Surge Modulates Nicotinic Receptors and Nicotine-Induced [3H]-Glutamate Release in Rat Cerebellum Slices," *JPET Fast Forward* 45625, it is reported that the [(3)H]-glutamate overflow induced by alpha7 nAChRs activation was higher during the dark phase (when melatonin is produced endogenously) and that the nocturnal increase in nicotine-evoked [(3)H]-glutamate release is imposed by a nocturnal surge of melatonin, as it is abolished when pineal melatonin production is inhibited by either maintaining the animals in constant light for 48 hours or by injecting propranolol just before lights off for two days; it is concluded that nicotine-evoked [(3)H]-glutamate release in rat cerebellum presents a diurnal variation, driven by the endogenous nocturnal pineal melatonin surge.

Markus, R. P. M., A, W. M. Zago, et al. (1996), "Melatonin modulation of presynaptic nicotinic acetylcholine receptors in the rat vas deferens," *The Journal of Pharmacology and Experimental Therapeutics* 279: 18-22, reported higher sensitivity to nicotine in prostatic portions incubated with exogenous melatonin, and in organs from animals killed at night, after the rise of endogenous melatonin, and concluded that this is probably due to the appearance of low-affinity neuronal nicotinic ACh binding sites.

The Markus articles appear to imply that melatonin enhances the effects of nicotine. If extrapolated to humans, the Markus results could explain the beneficial effects of melatonin during smoking cessation, in absence of exogenous nicotine administration, as demonstrated by Zhdanova. However, they would also imply that melatonin would exacerbate the nicotine-induced insomnia in smoking cessation, in subjects treated with nicotine.

Oral delivery of nicotine for therapeutic purposes has been proposed, e.g. in U.S. Pat. No. 6,183,775 (see below), as well as in WO8803803, WO02076211 and published US Patent Application 2001029959.

Published US Patent Applications 20030051728 and 20030062042 disclose methods of delivering a physiologically active compound (e.g. nicotine and melatonin among many others) as an aerosol.

U.S. Pat. No. 6,183,775 discloses a controlled release lozenge comprising active substances, among which are mentioned nicotine and melatonin.

U.S. Pat. No. 6,068,853 describes a transdermal delivery device for delivery of active agents, and mentions types, as well as specific instances, of active agents, e.g. melatonin and nicotine.

U.S. Pat. No. 5,284,660 describes a device which delivers drugs to the skin or to the mucosa at predetermined intervals. The deliverable drugs may be e.g., nicotine (for daytime administration) or melatonin (for nighttime administration). Neither this patent, nor any other of the patent documents (patents and published patent applications) mentioned herein, describe or suggest combined administration of nicotine and melatonin.

The entire contents of the patent documents (patents and published patent applications) mentioned herein are incorporated by reference in the present patent application.

It has now surprisingly been found, in relation to nicotine treatment, that exogenous melatonin produces a significantly greater benefit in insomnia patients who are habitual smokers compared to non-smokers. The synergistic effect of nicotine and melatonin on sleep has not been observed before, and is of potential utility in clinical interventions that involve nAChRs activation or particularly nicotine administration, to alleviate sleep problems incurred by these treatments. Besides, concomitant treatment by melatonin and nicotinic acetylcholine receptor modulation offers potentially significant benefits over nicotinic activation alone, in improving cognitive function in the elderly in general and in Alzheimer's disease patients in particular. Since sleep is important for memory consolidation (Maquet, P. (2001), "The Role of Sleep in Learning and Memory," *Science* 294: 1048-1052), concomitant melatonin-nicotinic therapy might also be expected to improve next day cognitive and memory functions due to enhanced sleep-dependent memory consolidation.

SUMMARY OF THE INVENTION

In general terms, the invention concerns the administration of melatonin and related compounds, either in regular or prolonged release dosage form (or any other form of administration) in order to treat nAChRs activation related insomnia (in smoking cessation as well as other medical indications), and for improvement of cognitive function and memory.

Thus, the present invention provides in one aspect, a pharmacologically active combination, having utility in treating insomnia patients, which comprises: (a) at least one first active ingredient selected from melatonin, other melatonergic agents, melatonin agonists and melatonin antagonists; and (b) at least one second active ingredient selected from nicotine and nicotine receptor agonists. In the pharmacologically active combination of the invention, components (a) and (b) may be formulated separately, or may be formulated together in a single formulation.

In another aspect, the invention consists of use of at least one first active ingredient (a) selected from melatonin, other melatonergic agents, melatonin agonists and melatonin antagonists, in the manufacture of a first medicament which alleviates at least one of the following adverse effects which occur in the patient in the course of nicotine replacement therapy, namely, impairment of the quality of sleep, impairment of cognition and impairment of memory, wherein said patient may optionally be receiving simultaneously a second medicament comprising at least one second active ingredient (b) selected from nicotine and nicotine receptor agonists.

In yet another aspect, the invention consists of use of at least one first active ingredient (a) selected from melatonin, other melatonergic agents, melatonin agonists and melatonin antagonists, in the manufacture of a first medicament which in the presence of a second medicament as defined below alleviates, in patients other than those receiving nicotine replacement therapy, at least one of the following adverse effects, namely, impairment of the quality of sleep, impairment of cognition and impairment of memory, wherein said second medicament comprises at least one second active ingredient (b) selected from nicotine and nicotine receptor agonists.

In still another aspect, the present invention provides a kit having utility in treating insomnia patients, which comprises:

(A) a first pharmaceutical formulation in unit dosage form comprising, in addition to at least one diluent, carrier or adjuvant, at least one first active ingredient selected from melatonin, other melatonergic agents, melatonin agonists and melatonin antagonists; and (B) a second pharmaceutical formulation in unit dosage form comprising, in addition to at least one diluent, carrier or adjuvant, at least one second active ingredient selected from nicotine and nicotine receptor agonists;

wherein the dosage units in (A) and (B) are independently selected from those adapted for oral, rectal, parenteral, transbuccal, intrapulmonary or transdermal administration.

DETAILED DESCRIPTION OF THE INVENTION

The pharmacologically active combination according to the invention, as well as each medicament in the uses of the invention, may be characterized by at least one of the following features:

(i) it comprises also at least one diluent, carrier or adjuvant;
(ii) it is in the form of dosage units, and the dosage units are adapted for oral, rectal, parenteral, transbuccal, intrapulmonary or transdermal administration;
(iii) it is a controlled, sustained or prolonged release formulation;
(iv) it is in a depot form which will release the active ingredients slowly in the body, over a preselected time period;
(v) ingredient (a) is melatonin;
(vi) ingredient (b) is nicotine;
(vii) it comprises at least one melatonin receptor modifier and/or melatonin profile modifier;
(viii) the first and second active ingredients (a) and (b) are formulated in a single formulation.

The pharmacologically active combination according to the invention, as well as each medicament in the uses of the invention, may be in the form of dosage units, wherein each dosage unit contains at least one of the active ingredients in an amount which lies within the range of 0.025-100, preferably 0.25 to 50 and more preferably 0.5 to 40 mg.

The kit provided by the present invention is preferably further characterized by at least one of the following features:
i) at least one of (A) and (B) is a controlled, sustained or prolonged release formulation;

ii) at least one of (A) and (B) is in a depot form which will release the active ingredients slowly in the body, over a preselected time period;
iii) said at least one first active ingredient comprises melatonin;
iv) said at least one second active ingredient comprises nicotine;
v) (A) comprises also at least one melatonin receptor modifier and/or melatonin profile modifier;
vi) (A) comprises also at least one further active ingredient selected from nicotine and nicotine receptor agonists;
vii) said first and second active ingredients, and said further active ingredient if present, are present in said dosage units in an amount which lies within the range of 0.025-100 mg, preferably 0.25 to 50 mg, more preferably 0.5 to 40 mg.

Without prejudice to the generality of this aspect of the invention, it is presently preferred that (A) and (B) are each in the form of a transdermal patch. Such a kit is exemplified, by way of illustration only, by a kit comprising the daytime and nighttime patches described in Formulation Example (C), below.

In another presently preferred embodiment of the kit of the present invention, (A) may be in the form of a controlled release tablet for oral administration and (B) in the form of a transdermal patch. Such a kit is exemplified, by way of illustration only, by a kit comprising the melatonin-containing tablets and the nicotine-containing patch described in Formulation Examples (A) and (B), below.

In accordance with the present invention, it was unexpectedly found that while melatonin levels in smokers and non smokers were comparable, administration of melatonin (controlled release 2 mg) daily in the evening for 4 weeks had a significantly greater effect on the improvement of sleep quality in smoking than non-smoking patients with insomnia aged 55 years and older over the values found with placebo treatment of the same individuals (e.g. as shown in Example 1).

In addition, administration of melatonin (controlled release 2 mg) daily in the evening for 3 weeks had a significantly greater effect in smoking than non-smoking patients with insomnia aged 20-55 years in the improvement of sleep quality (e.g. as shown in Example 2).

Moreover, administration of melatonin (controlled release 2 mg) daily in the evening for 3 weeks had a significantly greater effect in smoking than non-smoking patients with insomnia aged 55 years and over with respect to the enhancement of psychomotor skills (e.g. as shown in Example 3).

Even more surprising was the finding that a single administration of melatonin (controlled release 2 mg) resulted in a significantly improved memory recall over that under placebo treatment in the same subjects who were smokers or ceased smoking less then 6 months before the trial, compared to that in non-smokers (e.g. as shown in Example 4).

The invention will now be illustrated by the following non-limiting examples.

EXAMPLE 1

The effect of a controlled release formulation of melatonin on subjectively assessed sleep quality in 17 elderly insomnia patients (aged 66.9 (SD 5.4) years) were studied in a randomized, double-blind, crossover study. Basal excretion of the main melatonin metabolite 6-sulfatoxymentonin in urine over the nocturnal period (8 p.m.-8 a.m.) was measured and the subjects were treated for 1 week with placebo to establish baseline characteristics followed by a two-period crossover design (4 weeks on either melatonin controlled release 2 mg or placebo) separated by a washout period (1 week). On the last week of the baseline and treatment periods patients were asked to assess the quality of their sleep the previous night by ticking a 140 mm visual analog scale. The distance (in mm) of the patient mark from the left hand side of the scale was measured and a higher number indicated better sleep. The difference from placebo values in the patient evaluation of restful sleep was calculated for smoking and non-smoking patients. There were no significant differences in the amount of nocturnal 6-sulfatoxymentonin excreted by smokers and non-smokers in the study population (3.5+1.5 vs. 6.3+5 µg 6-sulfatoxymentonin, respectively). Surprisingly, it was found that the improvement in quality of sleep with melatonin over that with placebo was significantly greater in smokers showing a synergistic effect of the melatonin and nicotine (Table 1). No difference was found in the response to placebo between the smokers and non-smokers.

TABLE 1

Effects of melatonin over placebo on subjectively assessed quality of sleep in smoker and non-smoker insomnia patients.

| Parameter | Non smokers (n = 4) | Smokers (n = 10) | Significance (t-test) |
| --- | --- | --- | --- |
| Mean change (in mm) in perceived quality of sleep with melatonin over placebo | −2.8 | 15 | P = 0.003 |
| Mean nocturnal 6-sulfatoxymenlatonin excretion (µg/night) | 3.5 | 6.3 | P = 0.29 |

EXAMPLE 2

The effect of a controlled release formulation of melatonin on subjectively assessed sleep quality were studied in a mixed age insomnia patients population (aged 20-80 years). The subjects were treated for 1 week with placebo to establish baseline characteristics and then for 3 weeks with 1 mg per night of controlled release melatonin or placebo. On the last three days of the baseline and treatment periods patients were asked to assess the quality of their sleep the previous night using the Leeds Sleep Evaluation Questionnaire (Parrott, A. C. and I. Hindmarch (1980), "The leeds sleep evaluation questionnaire in psychopharmacological investigations—a review," *Psychopharmacology* (*Berl*) 71(2): 173-9) which comprises two 100 mm visual analog scales relating to sleep quality. The distance of the patient mark from the right hand-side in mm was measured and the mean answer of the two questions was averaged across the 3 consecutive nights. A responder was defined as a patient showing improvement of 10 mm or more on the averaged value. Surprisingly it was found that regardless of age there was a significantly higher rate of responders among the smokers (62%, n=16) than among the non-smokers (40%, n=43, p=0.002). There was no difference in responder rate to placebo between the smokers (46%, n=13) and non-smokers groups (44% n=53, p=0.89, chi-square test).

EXAMPLE 3

The effect of a controlled release formulation of melatonin on psychomotor performance (total reaction time, TRT, and Mean reaction time, MRT) in 40 elderly insomnia patients (aged 60.8 (SD 0.8) years) were studied. The subjects were treated for 2 weeks with placebo (baseline) and 3 weeks with 2 mg per night of controlled release melatonin. On the last two days of treatment psychomotor tests were taken by all patients to assess daytime vigilance. The improvement in Psychomotor skills in patients treated with melatonin were significantly higher in the smokers (−38.95 msec on TRT and −36.07 on MRT) compared to non-smokers group (−5.21 and 0.62 msec, p=0.05 and p=0.03, respectively).

EXAMPLE 4

The effect of melatonin (2 mg controlled release formulation) and placebo on memory recall (Rivermead story test) were assessed in 16 elderly volunteers (>55 years; aged 59 (SD 3.2) years). In a randomised, double-blind, crossover study the subjects were given a tablet of placebo in the evening to establish baseline and then a tablet of melatonin or placebo in a random order in the evening with one week with no treatment in between treatments. The Rivermead test was given to the patients at 2 and 12.5 hours after the administration of the tablet. Surprisingly, melatonin resulted in improvement of memory tasks in the first hours of its administration over the respective placebo values in the same subjects. Memory efficiency is increased with controlled release 2 mg melatonin for both recalls (immediate and delayed) in the subjects who were smoking or ceased smoking within the last 6 months prior to the study than non-smokers compared to baseline or crossover placebo.

TABLE 2

Mean number of recalled elements of the story and Difference from placebo of memory performance at 2 hours after intake of melatonin or placebo.

| Time after dosing | Smokers (n = 4) | Non-smokers (n = 12) | Significance (t-test) |
|---|---|---|---|
| Number recalls - Melatonin | 14.8 | 9.8 | P = 0.056 |
| Number recalls - placebo | 12.2 | 12.1 | P = 0.33 |
| Difference in recalls under melatonin and placebo | 3.5 | −2.41 | P = 0.043 |

Examples of non-limiting pharmaceutical formulations, which may be utilized in accordance with the present invention, are given below.

FORMULATION EXAMPLES (A) Controlled-Release Melatonin

Controlled-release formulations for oral administration were prepared by compressing in a 7 mm cylindrical punch, at 2.5 tons, after dry mixing of the powdered materials, namely, 2 mg melatonin (Lipomed Co., Switzerland) and acrylic resin carrier (Rohm Pharma), so that the product contained Eudragit® RSPO 35.3%, lactose 16.7%. calcium hydrogen phosphate 41.4%, talc 1.3%, magnesium stearate 4%, melatonin 1.3%. It may be tabletted to contain e.g. 1 mg or 2 mg melatonin.

(B) Formulation Containing Nicotine Only

In the present example a transdermal patch is made that can hold and deliver sufficient nicotine to be effective for a period of 24 hours. The patch is typically replaced once a day, and can be used for smoking cessation therapy or in other situations where systemic nicotine delivery is indicated. A melatonin tablet given at night is used to alleviate the insomnia caused by the nicotine therapy. Melatonin is provided during the night, preferably as a controlled release tablet such as that described in Formulation Example (A), above, that can hold and deliver sufficient melatonin to be effective for e.g. the nocturnal 8 hour period.

For preparation of 1 g of the patch adhesive matrix, acetone (0.21 g) isopropyl alcohol (0.023 g) and ethyl alcohol (0.117 g) were placed in a stirring tank and EUDRAGIT® E100 (0.422 g) was added in portions with stirring until completely dissolved. Dibutyl sebacate (0.19 g) was then added and stirring continued for 20 minutes, followed by succinic acid (0.038 g) with stirring, which was continued for 10 minutes. A solution of nicotine-loaded adhesive was made by adding 33 wt % liquid nicotine to the adhesive matrix solution, and stirring for 30 minutes. A layer of backing material grade 3M-1005 (100 cm$^2$) was spread in a tray and covered with the matrix mixture. The mixture was cast with a blade height set at 1500 ml. The dish was covered, and the matrix was left for the solvent to evaporate at room temperature. Patches with an area of 10 cm$^2$ were cut from the finished matrix. An inert release 3M-1512 liner was applied to the adhesive surface and removed immediately prior to application of the device to the skin. The amount of nicotine per patch was 33 mg to be delivered over the 24 hour period.

(C) Formulation Containing Both Nicotine and Melatonin

It is contemplated that the formulation of this Example will be used for nighttime delivery of sufficient amounts of nicotine and melatonin to be effective for a period of 8-12 hours (after which it is replaced), and that it would preferably be used in conjunction with a separate patch for daytime delivery of nicotine only over a period of 12-16 hours, for smoking cessation therapy or in other situations where systemic nicotine delivery is indicated without causing insomnia. The daytime patch is typically replaced after 12-16 hours, and may be prepared as described in example (B), above, except that the strength of the nicotine solution is 21 wt % instead of 33 wt %.

For preparation of 1 g of the nighttime patch adhesive matrix, acetone (0.21 g) isopropyl alcohol (0.023 g) and ethyl alcohol (0.117 g) were placed in a stirring tank and EUDRAGIT® E100 (0.422 g) was added in portions with stirring until completely dissolved. Dibutyl sebacate (0.19 g) was then added and stirring continued for 20 minutes, followed by succinic acid (0.038 g) with stirring, which was continued for 10 minutes. A solution of nicotine- and melatonin-loaded adhesive was made by suspending 23 wt % melatonin in 0.35 g of acetone/isopropyl alcohol/ethyl alcohol mixture (9:1:5) and adding 12 wt % liquid nicotine, adding the suspension to the adhesive matrix solution, and stirring for 30 minutes. A layer of backing material grade 3M-1005 (100 cm$^2$) was spread in a tray and covered with the matrix mixture. The mixture was cast with a blade height set at 2500 mµ. The dish was covered, and the matrix was left for the solvent to evaporate at room temperature. Patches with an area of 10 cm$^2$ were cut from the finished matrix. An inert release 3M-1512 liner was applied to the adhesive surface and removed immediately prior to application of the device to the skin. Each patch contained 12 mg of nicotine and 23 mg of melatonin to be delivered over the 8-12 hour nocturnal period.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The invention claimed is:

1. A method of treating a patient in the course of nicotine replacement therapy for the purpose of alleviating at least one adverse effect occurring in the patient in need thereof as a result of nicotine withdrawal, said adverse effect selected from the group consisting of impairment of cognition and impairment of memory; said method comprising the administration to said patient prior to bedtime of a first medicament comprising at least one active ingredient (a) melatonin; wherein said patient is receiving simultaneously a second medicament comprising a second active ingredient (b) selected from the group consisting of nicotine and nicotine receptor agonists.

2. The method according to claim 1, wherein each of said medicaments is characterized respectively by at least one of the following features:
   (i) at least one of said medicaments further comprises at least one diluent, carrier or adjuvant;
   (ii) at least one of said medicaments is in the form of dosage units, and said dosage units are adapted for oral, rectal, parenteral, transbuccal, intrapulmonary or transdermal administration;
   (iii) at least one of said medicaments is a controlled sustained or prolonged release formulation;
   (iv) at least one of said medicaments is in a depot form which will release said active ingredients slowly in the body, over a preselected time period;
   (v) said first and second active ingredients (a) and (b) are formulated in a single formulation.

3. The method according to claim 2, wherein each of said first and second medicaments is in the form of dosage units, wherein each said dosage unit contains at least one of said active ingredients in an amount which lies within the range of 0.025-100 mg.

4. The method of claim 3, wherein said amount lies within the range of 0.25-50 mg.

5. The method of claim 4, wherein said amount lies within the range of 0.5-40 mg.

6. A method of treating a patient in the course of nicotine replacement therapy for the purpose of alleviating at least one adverse effect occurring in said patient, said adverse effect selected from the group consisting of impairment of cognition and impairment of memory; said method comprising administering to said patient prior to bedtime of a first medicament comprising at least one active ingredient (a) melatonin wherein said patient is receiving simultaneously a second medicament comprising a second active ingredient (b) selected from the group consisting of nicotine and nicotine receptor agonists; wherein said first active ingredient is provided in a controlled, sustained or prolonged release formulation and wherein said second active ingredient is provided in the form of a transdermal patch.

7. The method of claim 6, wherein each of said medicaments is characterized by at least one of the following features:
   (i) at least one of said medicaments further comprises at least one diluent, carrier or adjuvant;
   (ii) at least one of said medicaments is in the form of dosage units, and said dosage units for said first active ingredient are adapted for oral, rectal, parenteral, transbuccal, intrapulmonary or transdermal administration;
   (iii) said first active ingredient (a) is formulated with said second active ingredient (b) in a single formulation.

8. The method of claim 7, wherein said first and second medicaments respectively are in dosage unit form, wherein each of said dosage units contains at least one of said active ingredients in an amount which lies within the range of 0.025-100 mg.

9. The method of claim 8, wherein said amount lies within the range of 0.25-50 mg.

10. The method of claim 9, wherein said amount lies within the range of 0.5-40 mg.

* * * * *